United States Patent [19]

Ikonomou et al.

[11] Patent Number: 5,349,186

[45] Date of Patent: Sep. 20, 1994

[54] ELECTROSPRAY INTERFACE FOR MASS SPECTROMETER AND METHOD OF SUPPLYING ANALYTE TO A MASS SPECTROMETER

[75] Inventors: Michael G. Ikonomou, Victoria; Paul Kebarle, Edmonton, both of Canada

[73] Assignee: The Governors of the University of Alberta, Edmonton, Canada

[21] Appl. No.: 83,714

[22] Filed: Jun. 25, 1993

[51] Int. Cl.$^5$ .............................................. H01J 49/10
[52] U.S. Cl. .................................................. 250/288
[58] Field of Search ............................ 250/288, 288 A

[56] References Cited

U.S. PATENT DOCUMENTS

| | | | |
|---|---|---|---|
| 4,861,988 | 8/1989 | Henion et al. | 250/288 A |
| 4,935,624 | 6/1990 | Henion et al. | 250/288 |
| 4,999,493 | 3/1991 | Allen et al. | 250/288 A |
| 5,170,053 | 12/1992 | Hail et al. | 250/288 |

OTHER PUBLICATIONS

Smith, R. D.; Loo, J. A.; Edmonds, C. G.; Barniaga, C. J. and Udseth, H. R., Anal. Chem. 1990, 62,882.
Smith, D. P. H., IEEE Trans. Ind. Appl. 1986, 1A-22, 527.
Ikonomou, M. G.; Blades, A. T.; Kebarle, P. J. Am. Soc. Mass Spectrom. 1991, p. 441.
Fernandez de la Mora, J.; Rossel-Liompart, J., Procedings of the 39th ASMS Conference on Mass Spectrometry and Allied Topics, Nashville, 1991, p. 441.
Taflin, D. C.; Zhang, S. H.; Allen, T.; Davis, E. J., AIChE Journal 1988 34, 1310.
Ikonomou, M. G.; Blades, A. T.; Kebarle, P., Anal. Chem. 1991, 63, 1989–1998.
Wong, S. F.; Meng, C. K.; Fenn, J. B., Phys. Chem. 1988, 92, 546.
(a) Smith, R. D., Barniaga, C. J. and Udseth, H. R., Anal. Chem. 1988, 60, 1948–52.
Chowdhury, S. K.; Katta, V. and Chait, B. T., Rapid Commun. Mass Spectrom. 1990, 4, 81.
Reid, N.; Buckley, J. A.; French, J. B.; Poon, C. C., Adv. Mass Spectrom. 1979, 8B, 1843.
Ikonomou, M. G.; Blades, A. T.; Kebarle, P., Anal. Chem. 1990, 62, 957.
Sunner, J.; Ikonomou, M. G.; Kebarle, P., International J. Mass Spectrometry and Ion Processes 1988, 82, 221.

Primary Examiner—Jack I. Berman
Attorney, Agent, or Firm—Frank J. Dykas; Craig M. Korfanta

[57] ABSTRACT

A novel electrospray interface provides high sensitivity and signal stability for mass spectrometric detection of analytes in solvents with high water content including 100% water. The electrospray capillary tip section is heated close to the boiling point of the solvent. An approximately 20° C. hotter airstream is also used. Its flow is coaxial and codirectional to the electrospray. With this arrangement, the analyte signal sensitivity and stability obtained with neat water is equal to that with neat methanol. The charged state (degree of protonation) of protonated peptides sprayed from neat water and the heated spray is essentially identical to that observed with unheated spray where the solvent was 80% methanol—20% water.

20 Claims, 11 Drawing Sheets

ELECTROSPRAY INTERFACE FOR MASS SPECTROMETER AND METHOD OF SUPPLYING ANALYTE TO A MASS SPECTROMETER

FIELD OF THE INVENTION

This invention relates to a method and apparatus for forming ions from a liquid, and in particular from a water based solvent.

BACKGROUND AND SUMMARY OF THE INVENTION

Electrospray interfaces are used to deliver charged ions in the gas phase to a mass analyzer, generally a mass spectrometer. In an electrospray interface for a mass spectrometer, a charged capillary tube delivers a stream of liquid solvent to a discharge point at one side of an ionization chamber. An oppositely charged plate forms an opposite side of the ionization chamber. The stream of liquid solvent forms a cone at the tip of the capillary tube, with the tip of the cone extending away from the capillary tube, as charged particles in the liquid at the tip of the capillary tube are attracted towards the charged plate. Charged droplets of opposite polarity to the polarity of the capillary tube separate from the liquid cone and drift downfield towards the charged plate. As the charged droplets drift towards the charged plate, the liquid evaporates, thus forming gas phase ions. An orifice in the charged plate admits the gas phase ions into the ion analyzer portion of the mass spectrometer where they are detected as an observable analyte signal. Further description of the ion forming process using conventional electrospray interfaces may be found in "Electrospray-Ion Spray: A Comparison of Mechanisms and Performance", Ikonomou, M. G., Blades, A. T. and Kebarle, P., Anal. Chem. 1991, 63, 1989-1998.

A useful discussion of prior art methods and apparatus for extracting ions from a liquid solvent stream as applied to the field of mass spectrometry is found in U.S. Pat. No. 4,935,624 to Henion et al, col. 1, line 24, to col. 18, line 18. That patent describes a thermally assisted electrospray interface (TAESI) that is intended to overcome then existing prior art problems.

As described in the Henion et al patent, it has been found advantageous to heat the liquid solvent stream in the capillary tube, and this has found utility in the treatment of liquid solvent streams having a moderate percentage of water.

In general, however, conventional electrospray mass spectrometry of neat aqueous (pure water) solutions is much less successful when compared to electrospray involving solvents like methanol, ethanol and acetonitrile. When pure water is used as a solvent, the analyte signal observed is relatively very unstable and the observed ion intensity at a given analyte concentration is low. Yet electrospray of aqueous solutions is very desirable particularly where analysis of proteins is involved, since water is a good solvent for proteins, such as in reverse phase high protonation liquid chromatography (HPLC) and capillary electrophoresis (Ewing, A. G.; Wallingford, R. A.; Olefirowicz, T. M., Anal. Chem. 1989, 61,292.)

R. D. Smith et al. (Anal. Chem. 1990, 62,882.) found a method with which they could electrospray aqueous solutions. In their "Liquid Sheath Electrode" they combine, at the capillary tip, an outer liquid sheath of methanol with the inner aqueous flow emerging from the capillary. Thus, the solvent sprayed is actually a water-methanol mixture which is amenable to electrospray. While the method appears to work well, it still remains desirable to develop a method with which aqueous solutions can be electrosprayed without premixing with methanol.

One of the factors leading to poor performance for water as solvent is well understood, but, nonetheless, the solution to the problem has not previously been found. P. P. H. Smith (IEEE Trans. Ind. Appl. 1986, 1A-22,527) has shown that the electric field, $E_{on}$, required for the onset of liquid instability at the capillary tip and thus for the onset of electrospray is given by eq. 1.

$$E_{on}=(2\gamma\cos\theta/\epsilon_o r_c)^{\frac{1}{2}} \qquad (1)$$

where $\gamma$ is the surface tension, $\theta = 49°$ is the half angle of the liquid cone (Taylor cone) at the capillary tip and $\epsilon_o$ and $r_c$ are the permittivity of vacuum and the radius of the capillary. Since water has a surface tension ($\gamma = 0.073$ N m$^{-2}$) which is more than three times higher than that of methanol ($\gamma = 0.023$ N m$^{-2}$), the $E_{on}$ for water is close to two times higher. Generally, for a stable spray one needs a potential that is some 200-300V above the onset potential and for water the potential that would have led to stable spray causes electrical breakdown in the ambient gas, air (Smith, D. P. H. above cited and Ikonomou, M. G.; Blades, A. T.; Kebarle, P., J. Am. Soc. Mass Spectrom. 1991, 2, 497.). Gas phase ions are then formed not only by the electrospray process but also by gas phase ionization due to corona discharge. While it is generally easy to distinguish with the mass spectrometer between electrospray ions and discharge ions, the presence of electric discharge, which can be intermittent in this voltage range, leads to an instability of the electrospray derived analyte signal. The analyte signal is also strongly depressed when a discharge current approaching 0.8 μA or higher is present. This appears from work previously done by the inventors (Ikonomou, M. G.; Blades, A. T.; Kebarle, P., J. Am. Soco Mass Spectrom. 1991, 2, 497).

The discharge can be suppressed by the application of SF$_6$ gas flow around the electrospray capillary tip. Suppression of the discharge with SF$_6$ was found to lead to stable analyte signals and an increase of the analyte ion intensity. However, the sensitivity still remained lower by a factor of about 4 relative to that observed with methanol, even though the total capillary current $l_c$ was essentially the same when water or methanol were used as solvents.

From their analysis of the problem, the inventors have determined that the lower yield of gas phase ions from the charged droplets for water relative to methanol could be due to various factors such as:

(a) Larger droplets for a given charge could be formed when water was sprayed. The initial size of the droplets is one of the most important parameters. The droplets should not only be close to the Rayleigh limit but also very small. Under these conditions droplets small enough to lead to ion evaporation into the gas phase may be generated only after a few Rayleigh explosions.

(b) For droplets of equal radius and equal charge, the rate of solvent evaporation and thus the time required to reduce the droplet size to where gas phase ion emission occurs, could be lower for water.

(c) For droplets of sufficiently small size, so that gas phase ion emission can occur, ion evaporation could be slower out of water relative to methanol droplets of same size and charge.

The recently proposed equation of due to Fernandez de la Mora (Fernandez de la Mora, J.; Hering, S.; Rau, N.;McMurry, P., J. Aerosol. Sci. 1989, 21, 169) with which the relative size of droplets can be predicted (eqtn. 2)

$$d \propto (pQ^2/\gamma)^{\frac{1}{3}} \qquad (2)$$

where d is the droplet diameter, p the density of the solvent and Q the flow rate, provides an answer to question (a). According to eq. 2 the ratio of droplet size at the same flow rate should be:

$$\frac{d(MeOH)}{d(HOH)} \approx \left( \frac{0.8}{1} \times \frac{0.073}{0.023} \right)^{\frac{1}{3}} = 1.36$$

Thus, according to eq. 2 MeOH should lead to somewhat larger droplets and this means that factor (a) could not be responsible for the lower ion yield from water.

No simple equation is known to the inventors regarding (b), particularly for droplets which are not stationary in the ambient gas. Expressions dealing with evaporation rates and key references can be found in Davis et al. (AIChE Journal 1988, 34, 1310). The most important single parameter appears to be the vapour pressure of the solvent. The vapour pressures at 20° C. are: $p(MeOH) \approx 100$ torr, $p(HOH) \approx 20$ torr. On this basis one would expect that MeOH droplets initially of equal size will reduce their size much more rapidly than water droplets.

In previous work by the inventors (the above cited work and also Ikonomou, M. G.; Blades, A. T.; Kebarle, P., Anal. Chem. 1991, 63, 1989–1998), question (c) is examined on the basis of the Iribarne model (Wong, S. F.; Meng, C. K.; Fenn, J. B., J. Phys. Chem. 1988, 92,546) for very small droplets, $r < 10^{-2}$ μm, and came to the conclusion that the rate of ion evaporation will be higher for methanol relative to water, when droplets of the same charge and radius are compared.

It appears therefore, that the factors (b) and (c) are responsible for the lower gas phase ion yield out of water droplets. On that basis one might expect that heating of the droplets will lead to better performance when water is used. However, as the Henion device has shown, heating of the droplets is not sufficient when pure water is used as the solvent.

It is known in itself to use heat to improve electrospray performance, as with the Henion patent and also as reported by Smith, R. D.; Barniaga, C. J. and Udseth, H. R., Anal. Chem. 1988, 60, 1948–52. Chowdhury, S. K.; Katta, V. and Chait, B. T., Rapid Commun. Mass Spectrom. 1990, 4, 81. and Reid, N.; Buckley, J. A.; French, J. B.; Poon, C. C., Adv. Mass Spectrom. 1979, 8B, 1843. However, the use of heat in these latter three articles was not introduced specifically for electrospray of water. Fenn et al. (Wong, S. F.; Meng, C. K.; Fenn, J. B., J. Phys. Chem. 1988, 92,546) have reported the use of drying gas, $N_2$, heated to 330°–350K. Comparative experiments demonstrating the utility of this procedure were not reported.

R. D. Smith et al. (Anal. Chem. 1988, 60, 1948–52) have used heated nitrogen (interface) gas at 70° C. flowing in a counter current to the spray, for the desolvation of the gas phase ions. The purpose of these experiments was different from that of the present invention.

Chait and coworkers (Chowdhury, S. K.; Katta, V. and Chait, B. T., Rapid Commun. Mass Spectrom. 1990, 4, 81.) used a heated capillary tube (80°–100° C.) to transfer electrospray from atmospheric pressure to the vacuum system of the mass spectrometer. The purpose was to desolvate the droplets and gas phase ions. The solvent used was a 50:50 methanol-water mixture. A capillary temperature of 85° C. was found to maximize the protonated peptide signals. Experiments with other solvent mixtures and neat water were not reported.

The inventors have developed a new, heated, interface having surprising utility particularly with pure water solvents but also with other solvents. The present heated electrospray interface is very different from those used in previous work known to the inventors. Furthermore, the present heated electrospray provides outstanding performance for electrospray of aqueous solutions as shown by comparisons with electrospray obtained without heating and with other solvents (methanol).

The inventors have found that by the surprising expedient of using an entraining flow of gas about the spray of solvent, the sensitivity of the electrospray interface with pure water as the solvent may be greatly increased.

Thus one aspect of the invention provides a heated capillary source or tube having heated gas flow channels disposed about the heated capillary source such that the channels supply a flow of gas that heats and entrains the liquid solvent. The liquid solvent should have a temperature within the capillary source that is close to its boiling point. Preferably, the flow of gas is atmospheric air at atmospheric pressure, and has a temperature greater than the boiling point of the liquid solvent. A sleeve or other gas flow entraining means is useful to ensure that the flow of gas is concentric to the liquid solvent spray.

In one aspect of the method of the invention, ion production from a liquid solvent spray of an electrospray interface is enhanced by heating and entraining the liquid solvent spray with a flow of gas that surrounds and entrains the liquid solvent spray. The liquid solvent is preferably heated within the capillary to a point where it is near the boiling point of the liquid solvent and the gas has a temperature that is higher than this, preferably at least 20° C. higher for acetonitrile or methanol based solvents and 50° C. for pure water.

An electrospray interface in which the electrospray capillary is heated and the liquid solvent sprayed from the capillary is heated by a hot air stream which is coaxial and in the same direction as the spray, provides excellent performance for solvents in which water is the major component, including 100% water. This meets a very much needed requirement for HPLC and capillary electrophoresis applications of electrospray.

The coaxial and codirectional gas flow improves, by convection, the transport of droplets and ions to the sampling orifice. The near boiling point temperature of the solution at the capillary leads to a lowering of the surface tension of water and thus a lowering of the capillary voltage required for the onset of the spray. The initial high temperature of the droplets when formed and the subsequent heat transfer from the heated air stream facilitate the evaporation of water from the droplets and lead to rapid shrinkage of the droplets to the Rayleigh limit. Droplets that have reached the ion evaporation radius r<0.01 μm produce gas phase ions more efficiently when hot.

These and further aspects of the invention are described in more detail in the next two sections, and claimed in the claims that follow.

BRIEF DESCRIPTION OF THE DRAWINGS

There will now be described a preferred embodiment of the invention, with reference to the drawings, by way of illustration, in which like numerals denote like elements and in which.

DETAILED DESCRIPTION OF PREFERRED EMBODIMENTS

Figure 1:
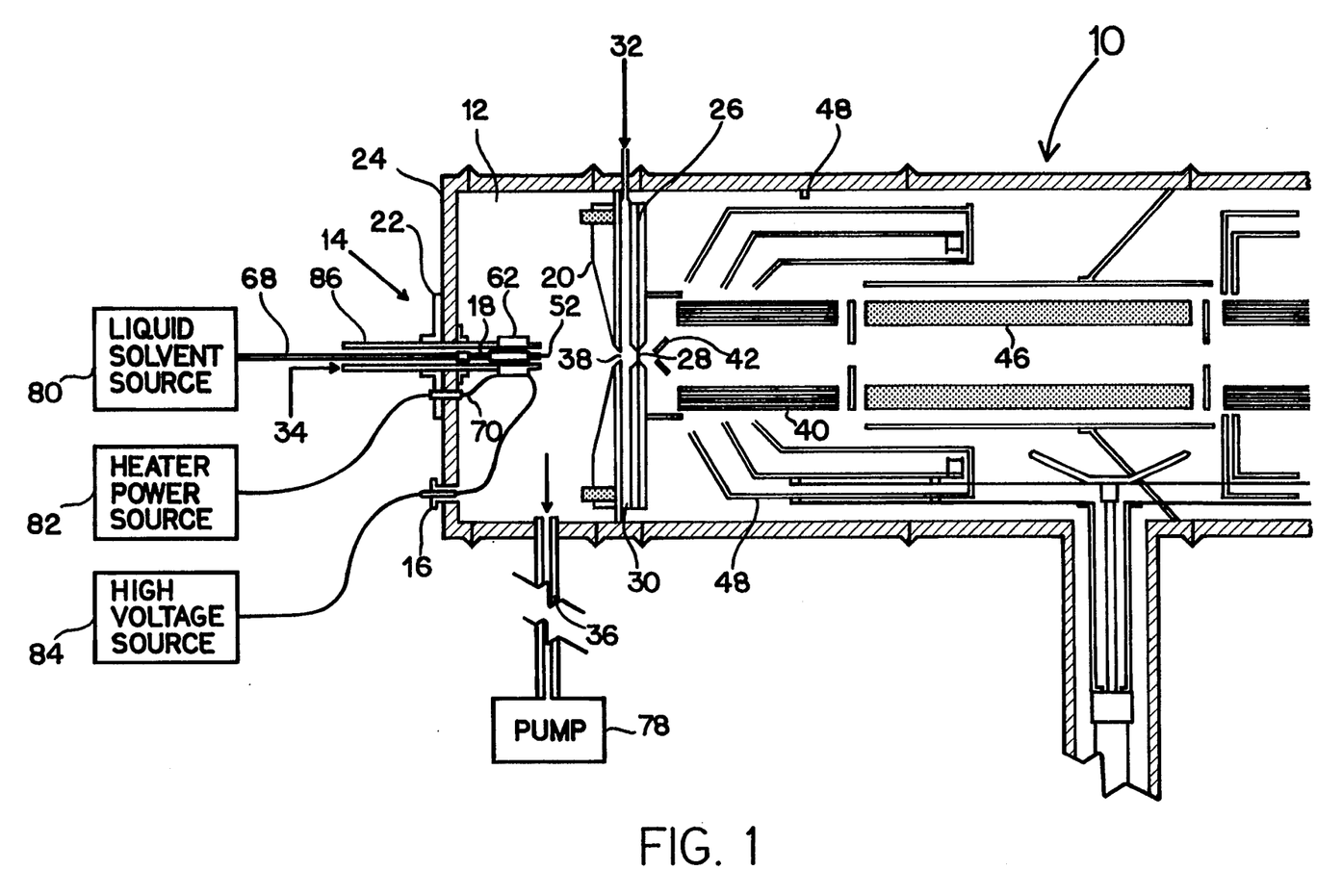
FIG. 1 is a schematic of the front end of a mass analyzer with electrospray interface according to the invention.
Figure 2A:
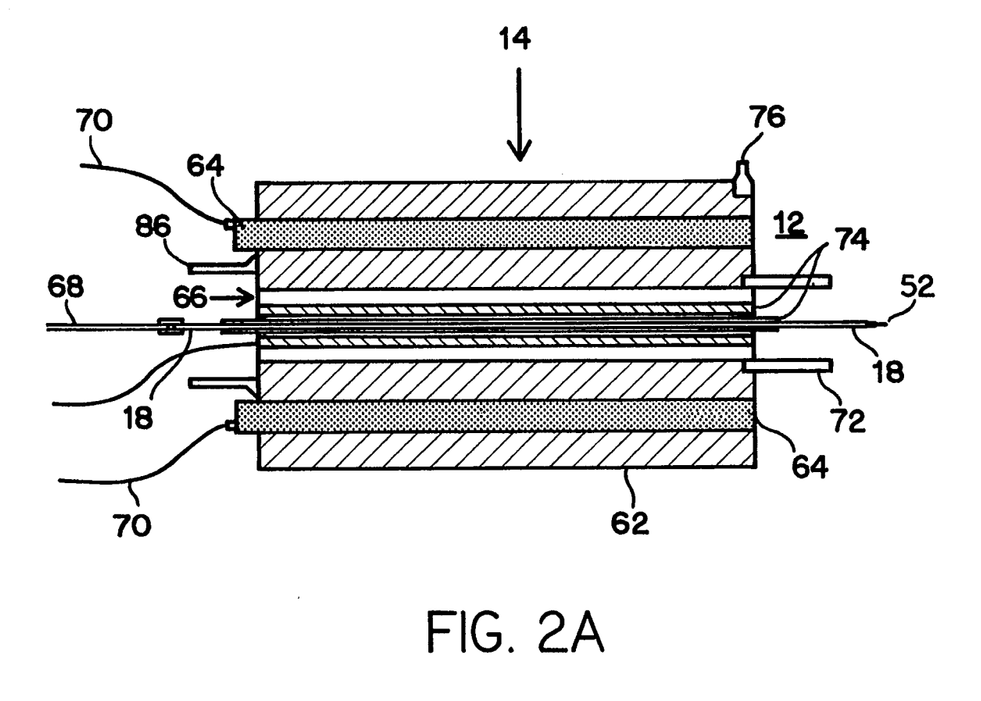
FIG. 2A is a longitudinal section of an electrospray interface according to the invention.
Figure 2B:
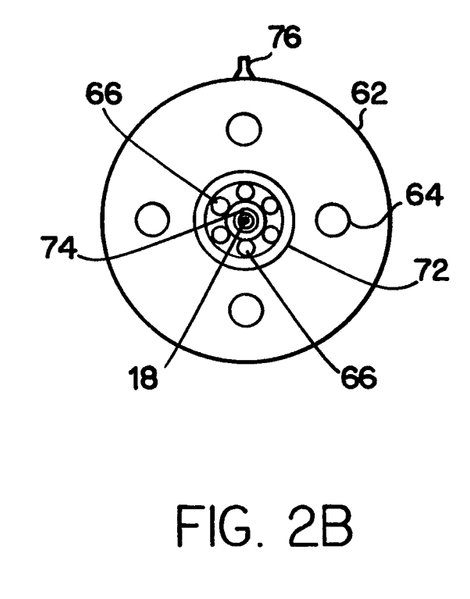
FIG. 2B is an end view of the electrospray interface of FIG. 2B.

Referring to FIG. 1, there is shown a mass spectrometer or mass analyzer 10 of conventional construction. Shown here as an example is the triple quadrupole mass spectrometer sold by Sciex Division of MDS Health Group Limited, of Thornhill, Ontario, Canada, under its trademark TAGA 6000E. At one end of the mass analyzer 10 is an atmospheric or ionization chamber 12, into which a heated electrospray generator (ESH) 14 according to the invention is mounted and of which a detailed schematic is shown in FIGS. 2A and 2B. The generator is preferably mounted for movement in three dimensions (x,y,z), as known in the art, using a holder plate 22 that is movably mounted on a transparent lucite lid 24. The chamber 12 is at atmospheric pressure, and in itself is known in the art. A pair of spaced plates, top plate 20 and bottom plate 26, are disposed across one end of the chamber 12 and define an interface chamber 30 between them that is supplied with ultrapure $N_2$ gas from a source 32. The top plate 20 and bottom plate 26 together separate the atmospheric ionization chamber 12 from the mass analyzer analysis section which is set at reduced pressure. A conducting capillary tube 18 that terminates in a tip or free end 52 is held by the holder 22 with the tip 52 disposed within the ionization chamber 12. A feed-through connection 16 is provided for electrospray voltage (4-6 kV) from a high voltage source 84 that is applied to the capillary tube 18, which thus functions as a charged electrode. The top plate 20 of the chamber 12 forms a counter electrode of the ionization chamber and a voltage of 650 V is applied to the top plate 20, thus establishing an electric field across the chamber 12 from the capillary tube 18 to the top plate 20 that induces liquid solvent to spray from the capillary tip 52 into the ionization chamber.

The top plate 20 includes a central 3.4 mm diameter orifice 38. The bottom plate 26 includes an orifice 28 having 115 μm diameter set in nickel foil. The nickel foil is set at a lower voltage (60 V) than the top plate (650 V), thus the gradient of the field continues past the bottom plate 26. An inlet port 34 and outlet port 36 in the chamber 12 allows circulation of atmospheric air into the chamber 12. Flow of nitrogen gas through the interface chamber 30 provides for the isolation of atmospheric air from the analysis section of the mass analyzer. Also shown in FIG. 1 are conventional components of a mass spectrometer including electrodes 40 forming a Brubaker lens, cluster buster electrode 42, first quadrupole 46 and cryopumping surfaces 48.

The free end or tip 52 of the capillary tube 18 is set about 3 cm from the top interface plate 20. Charged droplets sprayed by the heated electrospray generator 14, from the tip 52, drift downfield towards the top interface plate 20. The droplet current leaving the capillary 18 can be measured by an instrument and will be called $I_c$. Under ideal circumstances most of the charge on the droplets becomes converted to gas phase ions before the droplets reach the interface plate. A fraction of the ions and charged droplets that enter the interface chamber 30 through the 3.4 mm diameter orifice 38 in the top interface plate 20 drift through ultra pure $N_2$ gas at 1 atm. towards the bottom plate 26 of the interface chamber 30. Ions entering the interface chamber 30 are solvated by several solvent molecules (per charge) and desolvation (declustering) down to one or two solvent molecules occurs in the dry nitrogen between the orifices 28 and 38. Ions arriving near the central 115 μm orifice 28, located on a foil on the bottom interface plate 26, are entrained by gas flow provided by the electrospray interface 14 into the vacuum of the mass spectrometer.

An electrospray interface or electrospray generator 14 according to the invention is shown in FIGS. 2A and 2B. Disposed along the central axis of the electrospray interface is capillary tube 18. It will be understood that the capillary tube 18 must be designed in such a way as to allow charging of the liquid spray that emerges from the tip 52 of the capillary tube 18, and for this reason is preferably conducting and made of stainless steel, though it is not necessary that all of the tube be made conducting. The capillary tube is not necessarily cylindrical providing that it may function as a conducting capillary source. The capillary tube 18 is disposed within a heater, which is formed by a copper block 62 heated by several identical 70W cartridge heaters 64 disposed circumferentially about the block 62 in four channels formed in the copper block. The cartridge heaters 64 are connected via leads 70 to power source 82. The leads 70 pass through feed throughs in the holder 22.

Air flow channels 66 providing gas flow discharge into the ionization chamber are formed within the block 62 and are disposed circumferentially around the capillary tube 18. At one end of the block 62, the channels 66 are open to atmospheric air at inlet port 34 and at the other end the channels 66 discharge a spray entraining flow of air into the ionization chamber 12 that flows in the same direction as the spray of liquid solvent. Six channels 66 are used, spaced equally and circumferentially around the capillary tube 18, but the number and dimensions of the channels may be modified so long as an entraining flow of gas is provided. The inside diameter of the channels is about 1.6 mm. Silica tubing 68 supplies liquid solvent to one end of the capillary tube 18 from source 80.

Extending from the block 62 into the ionization chamber 12 and disposed about the capillary tube 18 and gas flow channels 66 is a stainless steel sleeve 72. The sleeve 72 has a 1.5 cm outside diameter, 1.2 cm inside diameter, and extends 1.2 cm from the copper block 62, thus forming an airflow guide for air flow discharging from the channels 66 into the ionization chamber 12. The sleeve 72 helps to ensure that the gas flow emerging from the channels 66 is smooth, parallel to and concentric to the spray emerging from the tip 52 of the capillary tube 18, thus forming an entraining flow of gas. The tip 52 extends about 1.5 cm beyond the sleeve 72.

To prevent overheating of the liquid solvent in the capillary tube 18, while keeping the temperature ($T_g$) of the flow of gas high one (FIG. 2B) or more (FIG. 2A) fused silica coaxial insulating tubes 74 are disposed coaxially about the capillary tube 18. The temperature $T_s$ of the liquid solvent in the capillary tube 18 should be maintained as close as possible to the boiling point of the liquid solvent by selection of the temperature of the heating block 62. This may be controlled in known fashion using the cartridge heaters 64. However, the temperature of the liquid solvent should not exceed the boiling point since otherwise pressurized vapour within the liquid, upon emerging from the tip 52, will disrupt the formation of small charged liquid droplets. At the same time, the temperature of the flow of gas exiting channels 66 should be higher than the temperature of the solvent and preferably higher than the boiling point of the liquid solvent, for example 20° C. higher for acetonitrile and methanol based solvents but preferably 50° C. higher for pure water as the liquid solvent, to ensure fast evaporation of the liquid solvent. A temperature differential between the liquid solvent and the flow of gas is therefore critical, and the insulation tubes 74 assist in maintaining the temperature differential with use of the same heater for heating the air flow and the liquid solvent.

The electrospray interface 14 is held in the wall of the ionization chamber 12 by a holder tube 86 secured within holder plate 22. The electrospray capillary 18 is made of stainless steel (ss) 0.2 mm outside diameter, 0.1 mm inside diameter and 9 cm long. The two coaxial silica tubes 74 are 1.5 and 3 mm outside diameter. As shown in FIG. 1, air flow through the channels 66 into the ionization chamber 12 and out into the atmosphere again is induced through a low pressure pump 78 or equivalent means, attached to the outlet 36 providing withdrawal of 0.5 L/s of air. The air comes in the inlet port 34 defined by the tube 86 and is distributed as a gas flow through the channels 66. Ambient air is preferred for the entraining gas but other gases may be used. The velocity of the air that has passed through the channels 66 is in the order of 5 m/s when it passes through sleeve 72 and the air passing through channels 66 is guided around the electrospray capillary tip 52 by means of sleeve 72. The velocity of the air through the channels 66 is substantially lower than a nebulizing speed.

A nebulizing speed as given in the Henion patent (U.S. Pat. No. 4,935,624 at col. 6, line 53), is in the order of 140–250 m/s although this will vary with the structure at the capillary tip 52. At a nebulizing speed, the gas flow around the tip 52 of the capillary 18 forces turbulent mixing of the gas with the liquid solvent droplets spraying from the tip 52, which disrupts the ion beam thus resulting in an unstable ion signal of reduced intensity. Furthermore, a gas flow above 7.5 m/s for the disclosed apparatus, drives small droplets into the interface chamber 30 and alters the ion chemistry and degree of solvation/dissolvation of the analyte and solvent ions, which is again not desired.

A nebulizing speed is therefore not desirable in this invention. Rather, the air flow should surround and entrain the liquid solvent. The spray of liquid solvent sprays from the tip 52 and normally spreads out laterally as it moves away from the tip. With the entraining flow of air, the air surrounds the spreading spray and tends to prevent it from spreading out. In this patent document, an entraining flow of gas is therefore a flow of gas that significantly hinders the spreading of the spray as it emerges from the capillary tip 18. The flow mass should also be high enough to entrain the spray. If the mass of the gas is too low, then the entraining effect will not be seen.

For the configuration of apparatus shown, wit analyte supplied at 10 μL/min., with a potential of 4.4 kV and the tip of the capillary 2.7 cm from the top plate 20, with the copper block at room temperature, the optimum volume flow rate is in the range of about 350 to 650 mL/s, which is equivalent to about 3.5 to 6.5 m/s velocity of the gas, with the optimum flow velocity for both methanol and water being around 5 m/s (500 mL/s). It has been found that for the disclosed apparatus, when the volume flow rate is increased to values higher than about 800 mL/s then there is a significant loss of signal intensity. The effect of a lower flow rate is not as marked, for flow rates down at least to 50 mL/s (0.5 m/s), although flow rates of around 0.01 L/s are believed inadequate. It is believed that the optimum flow rates do not depend on the temperature of the copper block.

For the experiments whose results are shown in FIG. 3–5, the temperature of the copper block was monitored with a thermocouple 76 attached to the block surface. The analyte solutions were transported from a syringe pump (not shown but well known in the art) to the electrospray capillary 18 via 50 μm fused silica tubing 68. The solution flow rate was 10 μL/min in all experiments discussed here. The heated electrospray generator was mounted to the atmospheric chamber via mounting tube 86 as shown in FIG. 1.

Mass analysis was obtained with the third quadrupole Q3, while Q1 and Q2 were operated in the RF only, total ion mode. The analytes were protonated bases $BH+$, obtained by dissolving the salts, generally BHCl, into the solvent.

The gas phase ions $BH+$ and $BH+(SL)$ where SL are solvent molecules passing through the orifice into the vacuum are in a cold supersonic jet and may experience growth to $BH+(SL)_n$. To prevent this, suitable accelerating potentials were applied to electrodes 42 (see FIG. 1), which lead to collisional activation of the ions and declustering to $BH+$.

Attempts were made to optimize several parameters. The optimization criteria used were maximum BH+ ion intensity and maximum ion signal stability. The size and geometry of sleeve 72, which directs the heated air flow over the capillary, the distance of the capillary tip 52 beyond the sleeve 72 and distance between capillary tip 52 and interface plate 20 given in the detailed description of the invention are believed optimum for the device given. However, routine experimentation may provide other acceptable values of the parameters. Potential applied to capillary 18 is $V_c$. Copper block potential is $V_{cu}$.

Figure 3A:
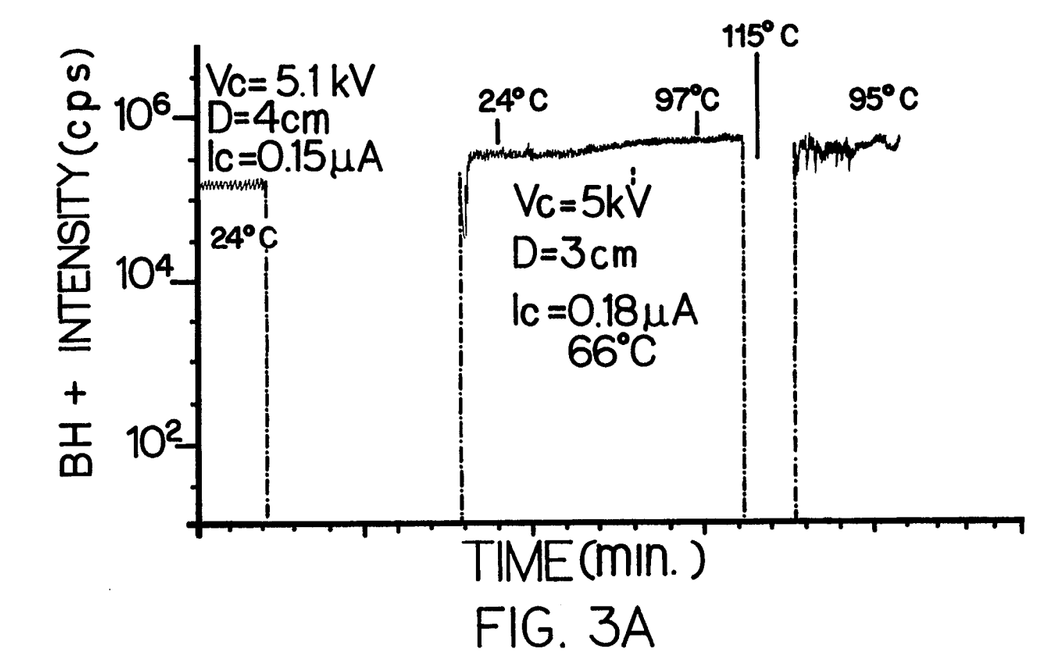
FIGS. 3A, 3B and 3C are graphs showing a single ion resolving (SIR) of BH+, analyte ion intensity, [BHCl]=$10^{-5}$ mol/L, B=cocaine, for various spray conditions, the voltage applied to the electrospray capillary being indicated in each of the Figures.

The ion intensity trace of the analyte ion BH+ obtained from electrospray of $10^{-5}$ mol/L BHCl in 100% methanol is shown in FIG. 3A, with $l_c=0.18$ $\mu$A. The trace at short time (0-2 minutes) was obtained with a conventional electrospray capillary (ES) which is of identical dimensions as the heat assisted capillary (ESH) shown in FIG. 2, but without the heater block and air stream. The BH+ trace for the electrospray capillary (8-16 minutes) was obtained for optimized parameters (D=4 cm, $V_c=6$ kV and off X=1.5 cm) where D gives the distance from the capillary tip to the interface plate, $V_c$ is the capillary potential and off X is the off axis distance between the capillary axis and the orifice of the interface plate.

The BH+ ion trace after 8 minutes shown in FIG. 3A was obtained with the heated electrospray generator at different block temperatures. The BH+ intensity with heated electrospray generator is higher by a factor of 2 even when heating is not applied (24° C.). The inventors attribute the higher signal to a directional focusing effect of the air flow. The directed flow which is coaxial to the capillary entrains the spray and reduces its angular divergence. It should be noted that the air flow velocity in the capillary tip region is not high enough to cause nebulization.

The application of heat increases the BH+ signal and a maximum is reached at 97° C. block temperature. Above this temperature, vapour was seen to escape from the capillary, an indication that the methanol was boiling. The current due to charged droplets leaving the capillary, $l_c$, as well as the mass analyzed current, BH+, go to zero under these conditions, see trace for BH+ at 16 min. in FIG. 3A.

Figure 3B:
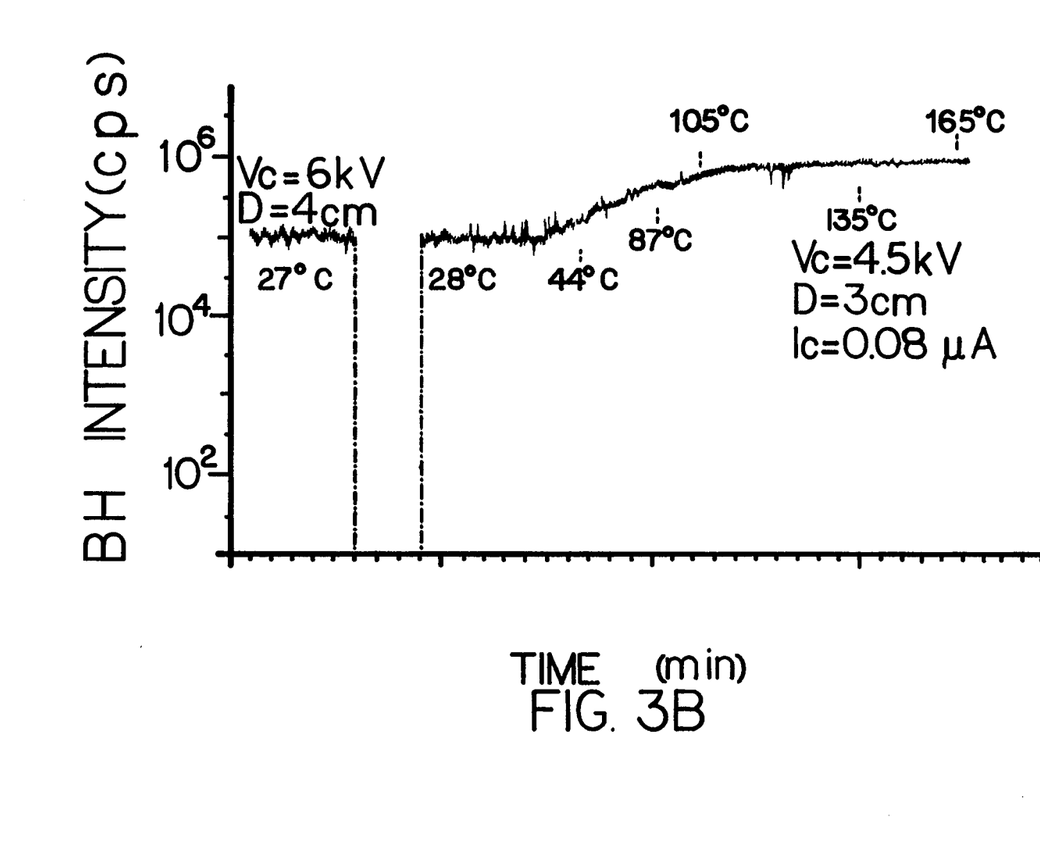

The BH+ intensity trace, when the solvent was a 50:50 mixture of methanol and water, is shown in FIG. 3B. The trace at short times (0-3 minutes) was obtained with the optimized electrospray capillary. The increase of BH+ intensity with temperature, obtained with the heated electrospray generator (4-20 minutes), is very much larger, by a factor of 10 at the optimum block temperature 135° C., than was the case for neat methanol. It is important to note also the excellent signal stability evident from the BH+ trace at higher temperatures.

Figure 3C:
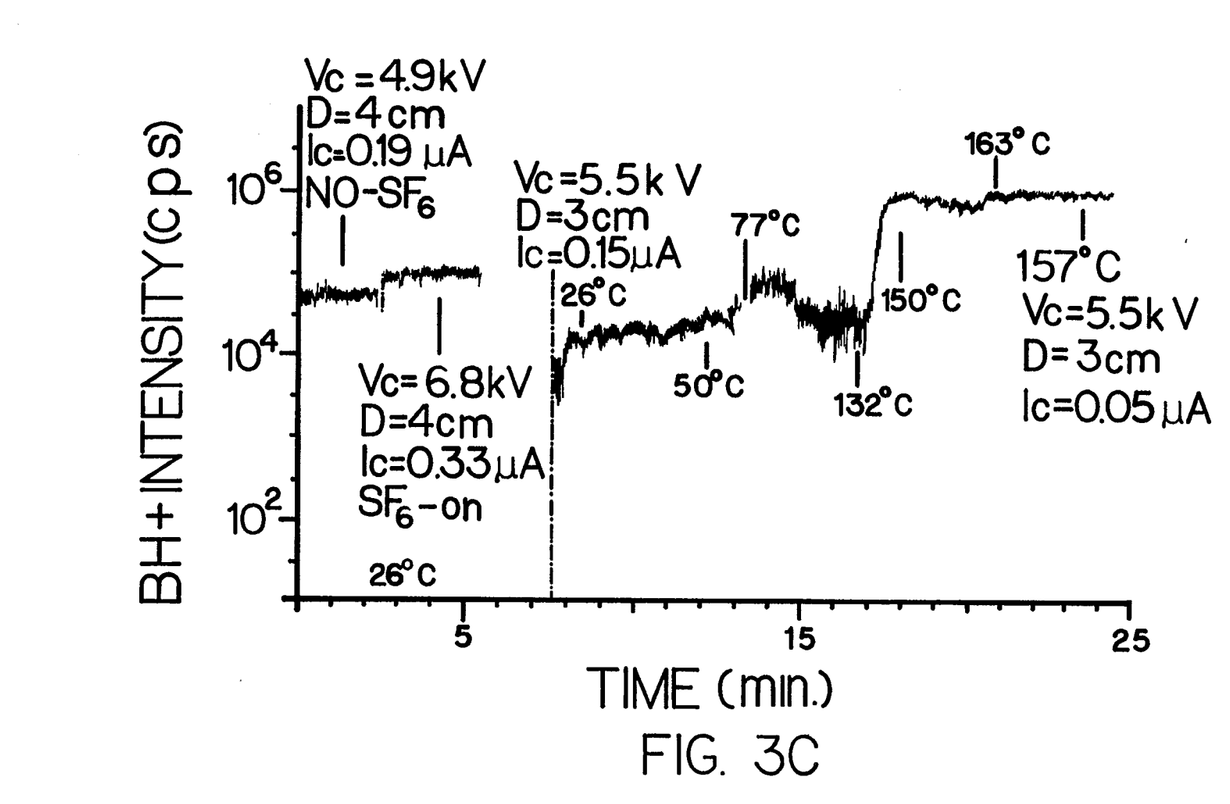

The BH+ intensity obtained with 100% water is shown in FIG. 3C. The trace at short times (2.5-5 minutes) was obtained with the electrospray capillary. In order to avoid a strong corona discharge, the capillary potential was kept relatively low, $V_c=4.9$ kV. A higher intensity is obtained at higher $V_c$ and $SF_6$ gas flow. The capillary used in this experiment has an axial outer tube (the inner of the tubes 74 may be used for this purpose) carrying $SF_6$ gas. The application of $SF_6$ flow at 0.4 L/min. allows a $V_c=6.8$ kV to be used. The BH+ signal stability is also better with $SF_6$. By far the best conditions are obtained with the heated electrospray generator (7-25 minutes), $l_c=0.055$ $\mu$A at 157° C.. Intermediate block temperatures, 30°-130° C. do not lead to a stable signal, see FIG. 3C. From 135° to 160° C. a very stable signal is obtained both with regard to short and long time constant, fluctuations. The BH+ signal at this intensity plateau is higher by a factor of 10 relative to the $SF_6$ assisted spray and by a factor of 20 relative to the electrospray capillary. Surprisingly, no $SF_6$ was required for the heated electrospray generator at these temperatures. No electric discharge was present in the absence of $SF_6$ even when the $V_c$ was 6 kV at D=3 cm. The absence of electric discharge can be deduced from the mass spectra obtained. These do not show abundant ions which are due to electric discharge, i.e. $H_3O+$ and $CH_3OH_2+$ core ions.

Figure 4:
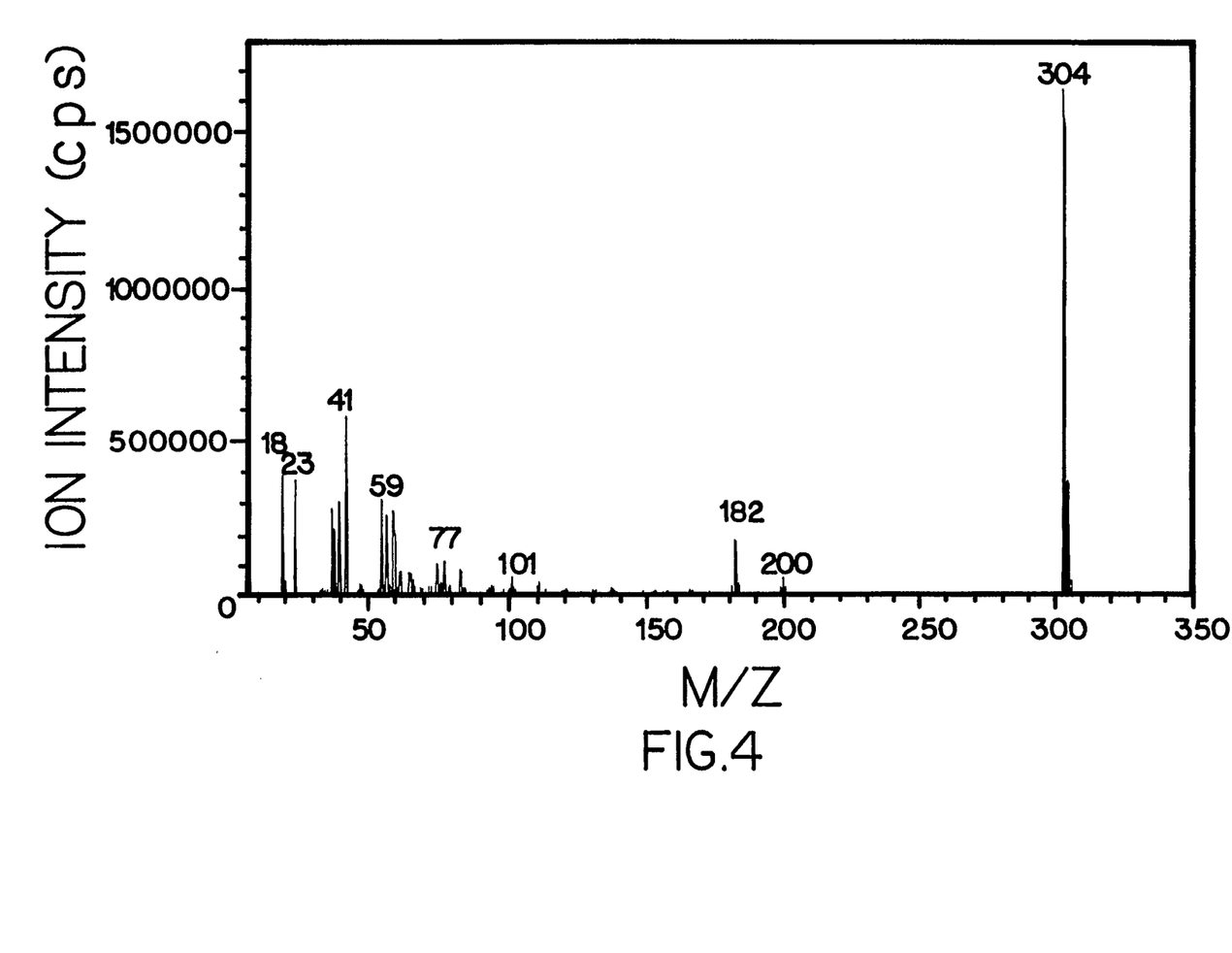
FIG. 4 is a mass spectrum obtained with the electrospray interface according to the invention obtained by electrospraying $10^{-5}$ mol/l cocaine/HCl dissolved in 100% $H_2O$.

A mass spectrum obtained with BHCl at $10^{-5}$ mol/L, where B=cocaine, in neat water with the heated electrospray generator is shown in FIG. 4, with the electrospray capillary at 5 kV, D=3 cm, copper block at 146° C., solution flow rate at 10 $\mu$L/min. The major peak of m/z=304 corresponds to BH+. The small m/z=182 and 200 peaks are due to collision induced dissociation of BH+ between electrodes 40 and 42, see FIG. 1, which occurs at the high potential drops selected in order to eliminate BH+$(H_2O)n$ clusters. The major extraneous ions, m/z=23, 41, 59, 77 corresponding to Na+$(H_2O)_n$ with n=0 to 3, are due to sodium salt impurities in water. Similarly m/z=18, $NH_4+$ is probably also due to an ammonium salt impurity. The ions $H_3O+$ and $H_3O+(H_2O)$ at m/z=19 and 37, which would indicate the presence of an electric gas discharge are absent. Thus, the mass spectrum demonstrates not only the exceptionally high analyte ion BH+ intensity but also the absence of electric discharge when heated electrospray generator is used with neat water as solvent.

The mass spectra obtained with neat water and either the conventional electrospray capillary, the $SF_6$ treated capillary and the unheated heated electrospray generator, contained discharge indicating ions. Furthermore, the capillary currents $l_c$ obtained, see FIG. 3, were considerably higher than the current observed for heated electrospray generator at high temperature. These current differences should be largely due to the absence of electric discharge with the heated electrospray generator at high temperature. Results for other analytes and comparisons with data obtained with neat methanol are given in Table 1.

Figure 5A:
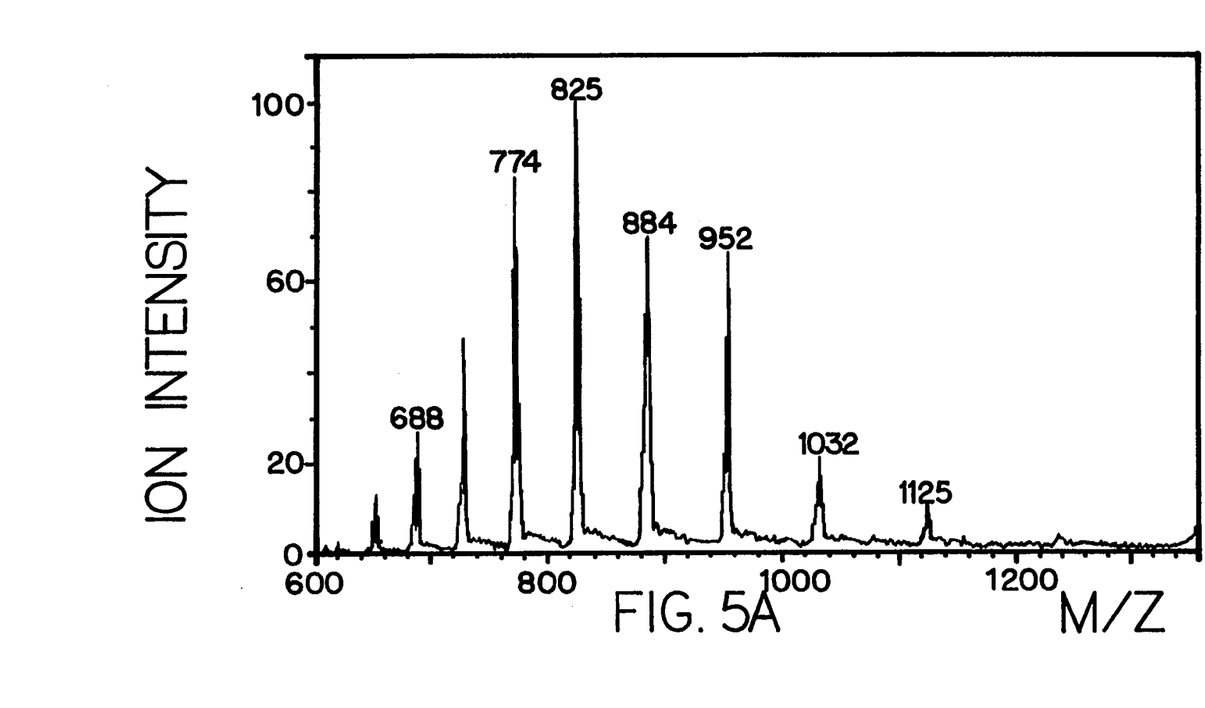
FIGS. 5A, 5B and 5C are mass spectra of cytochrome C (horses heart) using conventional electrospray (FIG. 5A) and an electrospray interface according to the invention (FIGS. 5B and 5C)
Figure 5B:
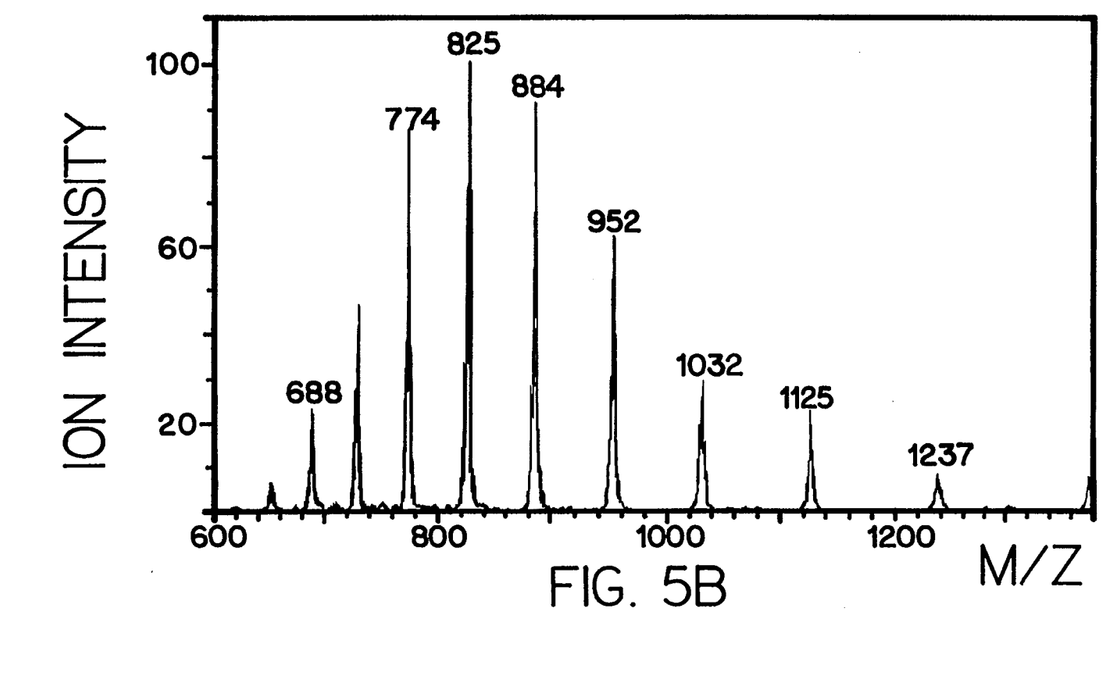

Shown in FIG. 5 are three mass spectra of Cytochrome C. The first spectrum A, was obtained with 80% MeOH, 20% $H_2O$ solvent with 0.8% formic acid and $6 \times 10^{-5}$ mol/L Cytochrome C sprayed at 10 $\mu$L/min with the conventional electrospray at 23° C. Spectrum B was obtained with the same solution and flow rates but with heated electrospray generator at 115° C. Notable is the fact that the relative abundances of the multiply protonated peptide ions are very similar in both cases even though the solution was exposed to a higher temperature when heated electrospray generator was used. The intensities obtained with the heated electrospray generator are higher by a factor of 3 relative to those from electrospray.

Figure 5C:
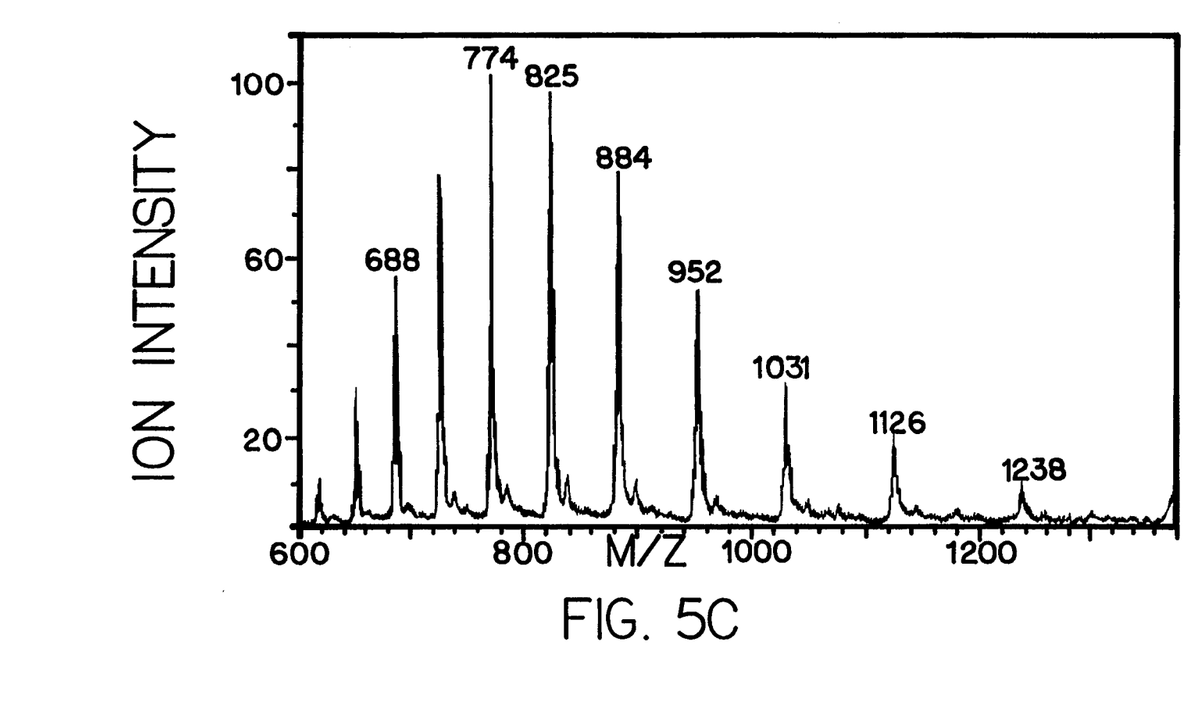

The mass spectrum obtained in FIG. 5C used neat water as solvent and 0.8% formic acid, $6 \times 10^{-5}$ mol/L Cytochrome C, 10 $\mu$L/minute flow and the heated electrospray generator device at 158° C. The peak distribution is very similar to that in the spectra shown in FIGS. 5A and 5B, but shifted very slightly toward lower protonation. The intensity obtained is similar to that obtained in spectrum of FIG. 5A, i.e. with 80% MeOH 20% H$_2$O and obtained with electrospray.

Similar results were obtained also with other peptides such as bradykinin. The degree of protonation did not change on using the heated electrospray generator and the sensitivity with neat water and heated electrospray generator was comparable to that with methanol and electrospray. Therefore, the heated electrospray generator device should be of great value for electrospray of reverse phase HPLC effluent and for Capillary Electrophoresis. In both of these cases, satisfactory column retention times are obtained only with high water content, H$_2$>80%, solvents which present significant difficulties for conventional electrospray devices.

The increased temperature of the solution flowing through the capillary obviously leads to a higher gas phase ion yield. One of the factors involved may be the change of surface tension $\gamma$. The temperature of the aqueous solution, at the tip of the capillary at optimum spray conditions was close to the boiling point 100° C. The surface tension of water decreases from $\gamma = 0.073$ N m$^{-2}$ at 29° C. to 0.059 N m$^{-2}$ at 100° C. From Smith's eq. 1 downward shift of the electrospray onset potential is expected at the higher temperature, but the effect is small:

$$V_{on}(100° C.)/V_{on}(20° C.) \approx \sqrt{0.059/0.073} = 0.91$$

Figure 6A:
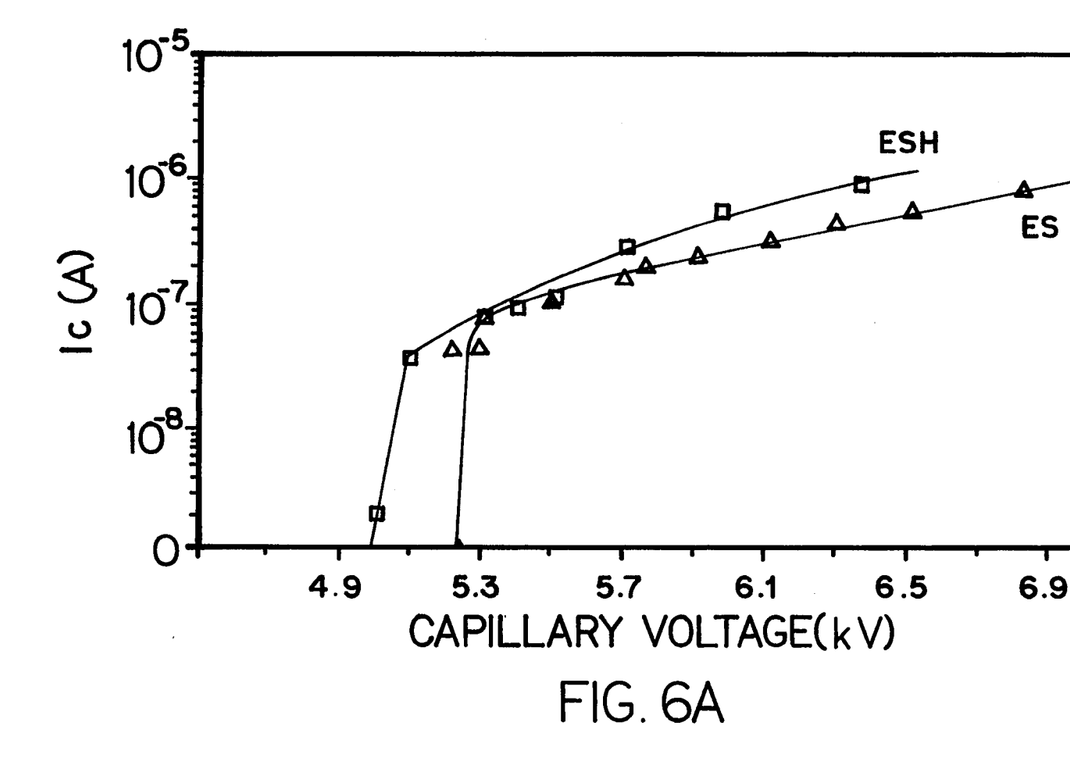
FIG. 6A is a plot of current due to charged droplets and gas phase ions leaving the electrospray capillary verses capillary voltage for conventional electrospray capillary at 29° C., and heated-electrospray assembly (ESH) at 140° C.
Figure 6B:
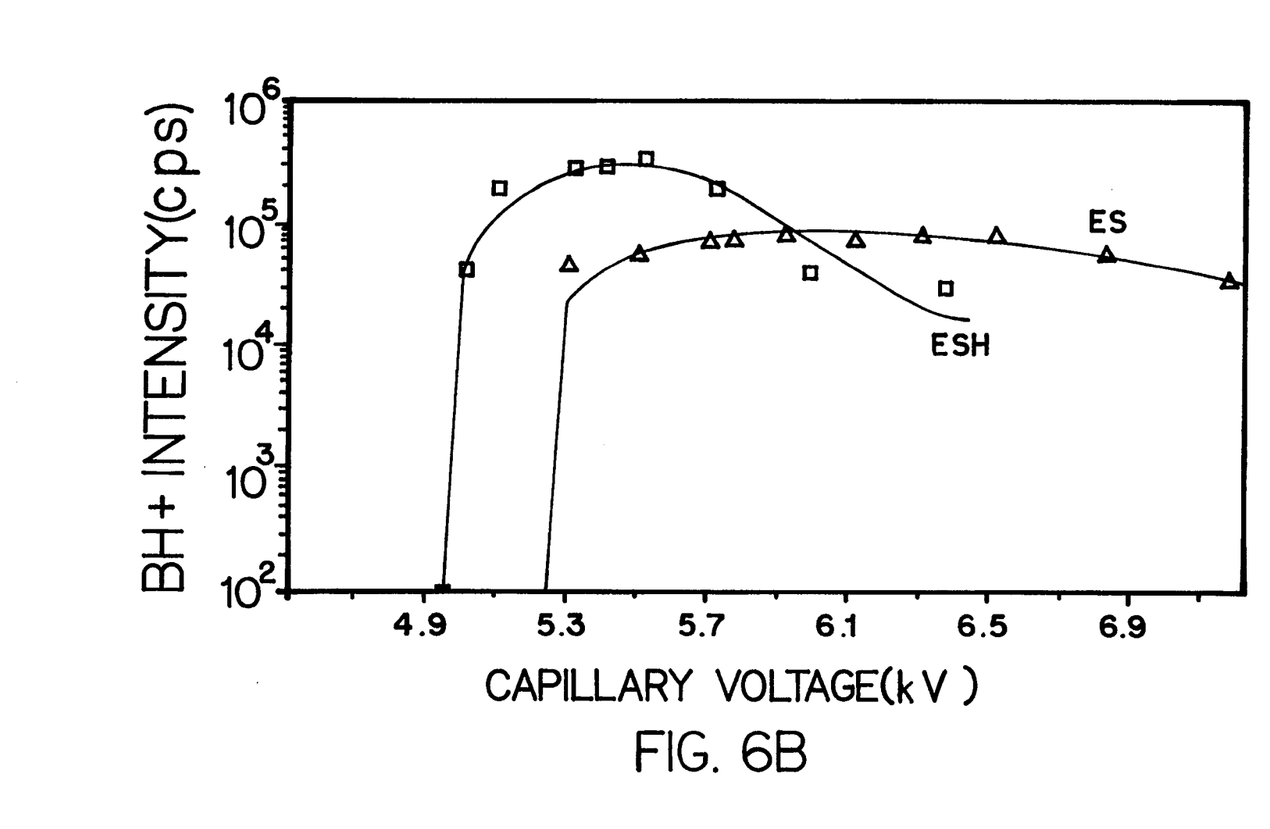
FIG. 6B shows current and mass analyzed analyte ion (BH+) versus capillary voltage for conventional electrospray capillary at 29° C., and heated-electrospray assembly at 140° C.

The measured onsets of spray current I$_c$ and mass analyzed BH+ ion current are shown in FIGS. 6A and 6B. [BHCl]=10$^{-5}$ mol/L where B=cocaine in 100% H$_2$O and solution flow rate 10 $\mu$L/min. Both currents indicate onsets at 4.3 kV(hot) and 4.6 kV(cold). These onsets were corrected by subtracting the 0.65 kV potential of the opposing electrode, that is, the top interface plate 20, see FIG. 1. These values lead to an experimental voltage ratio 0.93 about as predicted by eq. 1.

The observed onset voltage difference of 300 V indicates that the operating voltage with heated electrospray generator will be lower by 30 V relative to that for conventional electrospray. Therefore, a reduction of the electric discharge can be expected with the heated electrospray generator.

Since with heated electrospray generator, the droplets when formed will be already at a temperature near the boiling point, their rate of evaporation will be high from the instant of their formation. The time required for the heating up by the hot gas flow will thus be saved and more rapid evaporation rates will be achieved relative to the case where only a heated gas is used. Evidence that the evaporation of the droplets obtained with heated electrospray generator is much more complete is provided by the following observations. With conventional electrospray and neat water, the counter electrode (top interface plate 20) was wet, while with heated electrospray generator this electrode was completely dry. Also with the conventional electrospray a careful off axial positioning, of the spray tip 52 relative to the interface orifice 38 was required. When the off axis distance was too small (less than 1.5 cm), the observed mass analyzed ions were heavily clustered with solvent molecules. The inventors attribute this to droplet penetration of the interface gas when the stream is directed close to the orifice 38. With the heated electrospray generator no careful off axis positioning was required. The heated electrospray generator was often operated in axial alignment and the mass spectra indicated reasonably dry interface gas.

These results show that it is possible to spray water with the heated electrospray generator without electrical discharge at capillary potentials V$_c$ that are much higher than the 300 V gain expected from eq. 2 on the basis of the surface tension change. Observation of the liquid cone at the capillary tip 52 with a low power microscope revealed that the cone angle increased from a sharp angle, when the aqueous solution was cold to a much wider angle when the solution was hot. The liquid retreated much closer to the capillary tip and the spray became much finer. The fine spray had the same appearance as the spray obtained with room temperature methanol which leads to high ion intensities and a stable signal. A drop of capillary current I$_c$ by a factor of 3 occurred simultaneously with the change over to the fine water spray, see FIG. 3C. The inventors attribute this current decrease to a decrease of electric discharge. As mentioned above, the unheated water spray spectra contained electric discharge indicating ions and these ions were not present with the heated electrospray generator spray. The decrease of the discharge thus seems associated with the change over from a sharp to a blunt liquid tip spray. One would usually assume that discharges initiate at sharp metal points at or near the capillary rim. However, the rim was wetted by the liquid. Under these circumstances initiation of a discharge by a sharp liquid tip becomes a distinct possibility.

It is known from previous work done by the inventors that an electric discharge occurs at a lower capillary potential (4.5 keV) for water relative to methanol (5.5 keV) when both are sprayed under conventional, room temperature conditions with the same capillary. The change over from a sharp to a blunt liquid cone (fine) spray occurs for methanol below 4.5 kV and this is probably due to the lower surface tension of methanol. It is likely that the presence of a blunt cone allows one to increase V$_c$ to values well above 4.5 kV without initiation of discharge. On the other hand, for water, at room temperature, the sharp tip persists up to 4.5 kV and its presence at this high voltage could be associated with discharge initiation.

One explanation for the shift to a blunt tip for the heated water may be that even though the surface tension change on heating of water is small, it is just large enough to shift the sharp to blunt tip conversion to a voltage where discharge initiation is still not present. Once the blunt tip has occurred, the system can tolerate considerably higher potentials without discharge initiation.

Another explanation for the ability to electrospray water at near boiling temperature can be considered also. It is known that the rate of formation of vapour nuclei in the liquid increases rapidly with temperature. A high rate of vapour nucleation in the presence of the additional stress by the electric field at the liquid tip may be expected to assist droplet formation. The resulting droplet size in this vapour nucleation assisted spray may be much smaller. The more facile and rapid droplet formation may lead to a blunter liquid cone sooner and thus a reduced tendency towards an electric discharge. The charge to mass ratio of the droplets under gas nucleation assist may be lower, and assuming that the droplet diameter is much smaller, the gas phase ion yield per charge on the droplet can be expected to be much higher.

ALTERNATIVE EMBODIMENTS

A person skilled in the art could make immaterial modifications to the invention described and claimed in this patent document without departing from the essence of the invention.

TABLE I

Some representative intensities of mass analyzed ions observed with different spray devices and solvents.

| cone[a] Analyte/ | $BH + \frac{m}{z}$ [b] | Intensity kilo counts per sec.[c] | | | |
|---|---|---|---|---|---|
| | | ES 25° Methanol | ESH 25° Methanol | ESH 97° Methanol | ESH 157° Water |
| Cocaine HCl | 304 | 350 | 875 | 1200 | 1800 |
| Codeine HCl | 300 | — | — | 1500 | 1400 |
| Fyrosine HCl | 182 | 52 | 190 | — | — |
| Cytidine HCl | 123[d] | — | — | 140 | 60 |
| Inosine HCl | 137[d] | 15 | 33 | 96 | 25 |

[a]Analyte at concentration of $10^{-5}$ mol/L in sprayed solution.
[b]m/z of protonated base BH+ except when otherwise noted.
[c]Intensities of mass analyzed ions for different spray arrangements and solvents.
[d]doubly protonated base.

The embodiments of the invention in which an exclusive property or privilege is claimed are defined as follows:

1. An electrospray interface for use with a mass analyzer requiring an ion source, the mass analyzer having an ionization chamber, the interface comprising:
   a conducting capillary source having a free end for spraying a liquid solvent spray into the ionization chamber, the liquid solvent having a temperature $T_s$ lower than the boiling point of the liquid solvent; and
   heated gas flow discharge means for discharging a spray entraining flow of gas into the ionization chamber adjacent to the liquid solvent stream, the flow of gas having a temperature $T_g$ higher than $T_s$.

2. The electrospray interface of claim 1 in which the heated gas flow discharge means includes a heater for heating the flow of gas to a temperature $T_g$ higher than the boiling point of the liquid solvent.

3. The electrospray interface of claim 2 in combination with the mass analyzer, the free end of the capillary discharge source being disposed within the ionization chamber of the mass analyzer.

4. The electrospray interface of claim 3 in which the conducting capillary source is a capillary tube, and the heated gas flow discharge means includes a plurality of gas flow channels disposed circumferentially around the capillary tube, the heater being disposed about the gas flow channels; and means for inducing a flow of gas into the gas flow channels.

5. The electrospray interface of claim 4 further including insulation disposed between the gas flow channels and the capillary tube.

6. The electrospray interface of claim 5 in which the channels are open to the atmosphere and the gas is air.

7. The electrospray interface of claim 6 in which the means for inducing a flow of gas into the gas flow channels is a vacuum pump attached to the ionization chamber.

8. The electrospray interface of claim 7 further including a sleeve extending from the heater and disposed concentrically about the capillary tube and the gas flow channels.

9. The electrospray interface of claim 1 in which the liquid solvent is pure water.

10. A method of supplying analyte carried by a liquid solvent stream to a mass analyzer having an ionization chamber, the method comprising the steps of:
    spraying the liquid solvent into the ionization chamber at a temperature $T_s$ lower than the boiling point of the liquid solvent; and
    entraining and heating the liquid solvent with a flow of gas adjacent to the liquid solvent spray, the gas having a temperature $T_g$ higher than $T_s$.

11. The method of claim 10 in which $T_g$ is higher than the boiling point of the liquid solvent.

12. The method of claim 11 in which $T_g$ is at least 150° C. and the liquid solvent is pure water.

13. The method of claim 11 in which $T_g$ is at least 20° C. greater than the boiling point of the liquid solvent.

14. The method of claim 11 further including differentially heating the liquid solvent stream and the flow of gas with the same source of heat.

15. The method of claim 10 in which the liquid solvent is pure water.

16. The method of claim 11 in which the liquid solvent is pure water.

17. A method of supplying analyte carried by a liquid solvent stream to a mass analyzer having an ionization chamber, the electrospray interface including a charged capillary source having opposed ends, and the ionization chamber including an oppositely charged plate having an orifice, the method comprising the steps of:
    supplying liquid solvent to one end of the capillary source, the other end of the capillary source being disposed in the ionization chamber and spaced from the charged plate;
    applying a spray inducing charge to the capillary source and to the charged plate, whereby liquid solvent spray is induced to spray from the capillary source into the ionization chamber;
    heating the liquid solvent to a temperature lower than the boiling point of the liquid solvent; and
    providing a codirectional non-nebulizing flow of gas surrounding the liquid solvent spray, the codirectional flow of gas having a temperature at least 20° C. greater than the temperature of the liquid solvent.

18. The method of claim 17 further including differentially heating the liquid solvent and the flow of gas with the same source of heat.

19. The method of claim 17 in which the capillary source is surrounded by channels open to atmospheric air and providing the flow of gas includes:
    pumping air from the ionization chamber from a first port and thereby inducing air to flow through the channels.

20. The method of claim 17 in which the liquid solvent is water and further including heating the flow of gas to a temperature of at least 150° C.

* * * * *